US012256953B2

(12) United States Patent
Bruse

(10) Patent No.: US 12,256,953 B2
(45) Date of Patent: Mar. 25, 2025

(54) SURGICAL CLAMP FOR LAPIDUS BUNION SURGERY

(71) Applicant: Jason Bruse, Kaysville, UT (US)

(72) Inventor: Jason Bruse, Kaysville, UT (US)

( * ) Notice: Subject to any disclaimer, the term of this patent is extended or adjusted under 35 U.S.C. 154(b) by 709 days.

(21) Appl. No.: 17/394,319

(22) Filed: Aug. 4, 2021

(65) Prior Publication Data

US 2022/0039816 A1    Feb. 10, 2022

Related U.S. Application Data

(60) Provisional application No. 62/706,176, filed on Aug. 4, 2020.

(51) Int. Cl.
*A61B 17/28*    (2006.01)
*A61B 17/56*    (2006.01)
*A61B 17/88*    (2006.01)

(52) U.S. Cl.
CPC ........ *A61B 17/282* (2013.01); *A61B 17/2816* (2013.01); *A61B 17/2833* (2013.01); *A61B 17/2841* (2013.01); *A61B 17/8861* (2013.01); *A61B 2017/565* (2013.01)

(58) Field of Classification Search
CPC .............. A61B 17/282; A61B 17/2816; A61B 17/2833; A61B 17/2841; A61B 17/8861; A61B 2017/565; A61B 17/66; A61B 17/8866; A61B 17/1775
See application file for complete search history.

(56) References Cited

U.S. PATENT DOCUMENTS 5,578,032 A * 11/1996 Lalonde ............... A61B 17/282
606/205
2020/0138491 A1* 5/2020 Brigido .................. A61B 17/84

FOREIGN PATENT DOCUMENTS

CN        2267770 Y  * 11/1997
DE        20318554 U1 * 3/2004  ........... A61B 17/282

OTHER PUBLICATIONS

English Language Translation of DE 20318554U1 obtained from Espacenet Global Dossier. Published in German Feb. 19, 2004. (Year: 2004).*
English Language Translation of CN2267770Y obtained from Espacenet. Published in China Nov. 19, 1997. (Year: 1997).*
(Continued)

*Primary Examiner* — Tan-Uyen T Ho
*Assistant Examiner* — Cherie M Poland
(74) *Attorney, Agent, or Firm* — Kunzler Bean & Adamson

(57) ABSTRACT

Apparatuses, systems, and methods are disclosed for a surgical clamp for Lapidus bunion surgery. A surgical clamp has handles disposed at opposing branches of a surgical clamp. A hinge is disposed at an intersection of the opposing branches about which the opposing branches pivot. A first gripper is disposed at a distal portion of the first opposing branch and is shaped to hook around and grip a neck of a first metatarsal. A second gripper is disposed at a distal portion of the second opposing branch and is shaped to hook around and grip a neck of a different metatarsal. The grippers extend at a non-zero angle away from the opposing branches. A lock extends between the opposing branches and selectively fixes a relative position of the opposing branches so that the grippers selectively hold a position of the first metatarsal relative to the different metatarsal.

20 Claims, 6 Drawing Sheets

(56) References Cited

OTHER PUBLICATIONS

Rolian et al., (2010) The coevolution of human hands and feed. Evolution 64, 1558-1568. (Year: 2010).*
Dictionary.com—definition of forming. Last accessed Apr. 19, 2024. (Year: 1995).*
Dictionary.com—definition of disposing. Last accessed Apr. 19, 2024. (Year: 1995).*

* cited by examiner

SURGICAL CLAMP FOR LAPIDUS BUNION SURGERY

CROSS-REFERENCES TO RELATED APPLICATIONS

This application claims the benefit of United States Provisional Patent Application No. 62/706,176 entitled "SURGICAL CLAMP FOR LAPIDUS BUNION SURGERY" and filed on Aug. 4, 2020, for Jason Bruse, which is incorporated herein by reference.

TECHNICAL FIELD

This disclosure relates to surgical devices and more particularly relates to surgical clamps for Lapidus bunion surgery.

BACKGROUND

Lapidus bunion surgery may be performed to treat a bunion deformity, also known as hallux valgus. It may involve fusing the joint between the first metatarsal bone and one of the small bones in the midfoot called the medial cuneiform. It can be difficult to position and hold the first metatarsal bone in a proper corrected position during a Lapidus bunion surgery. The bone may need to be moved, and held in the proper place, temporarily during the surgery, until permanent fixation is applied. Devices may get in the way of other surgical instruments during surgery and may not allow for motion of the great toe joint, or the like. For example, surgical clamps can be too large and the shapes of the tips of the clamps do not fit the bones in this surgery.

SUMMARY

Surgical clamps for Lapidus bunion surgery are disclosed. In some embodiments, first and second opposing handles are disposed at a proximal portion of opposing first and second branches of a surgical clamp. A hinge, in certain embodiments, is disposed at an intersection of the opposing branches about which the opposing branches pivot in response to actuation of the handles. In one embodiment, a first gripper is disposed at a distal portion of the first opposing branch and is shaped to hook around and grip a neck of a first metatarsal. A second gripper, in a further embodiment, is disposed at a distal portion of the second gripping branch and is shaped to hook around and grip a neck of a different metatarsal. The first and second grippers, in one embodiment, extend at a non-zero angle away from the opposing branches. In certain embodiments, a lock extends between the opposing branches and selectively fixes a relative position of the opposing branches so that the first and second grippers selectively hold a position of the first metatarsal relative to the different metatarsal.

Apparatuses for Lapidus bunion surgery are disclosed. In one embodiment, an apparatus includes means for pivoting opposing first and second branches of a surgical clamp about an axis from a proximal end of the opposing first and second branches. An apparatus, in a further embodiment, includes means for hooking around and gripping a neck of a first metatarsal from a distal end of the first branch at a non-zero angle with the first branch. In certain embodiments, an apparatus includes means for hooking around and gripping a neck of a different metatarsal from a distal end of the second branch at a non-zero angle with the second branch. An apparatus, in some embodiments, includes means for selectively fixing a relative position of the opposing branches and for selectively holding a position of the first metatarsal relative to the different metatarsal.

Methods for Lapidus bunion surgery are disclosed. A method, in one embodiment, includes forming first and second opposing handles at a proximal portion of opposing first and second branches. A method, in a further embodiment, includes disposing a hinge at an intersection of the opposing branches about which the opposing branches pivot in response to actuation of the handles. In certain embodiments, a method includes forming a first gripper at a distal portion of the first opposing branch that is shaped to hook around and grip a neck of a first metatarsal. A method, in some embodiments, includes forming a second gripper at a distal portion of the second opposing branch that is shaped to hook around and grip a neck of a different metatarsal. The first and second grippers, in one embodiment, extend at a non-zero angle away from the opposing branches. A method, in certain embodiments, includes forming a lock extending between the opposing branches to selectively fix a relative position of the opposing branches so that the first and second grippers are configured to selectively hold a position of the first metatarsal relative to the different metatarsal.

BRIEF DESCRIPTION OF THE DRAWINGS

In order that the advantages of the disclosure will be readily understood, a more particular description of the disclosure briefly described above will be rendered by reference to specific embodiments that are illustrated in the appended drawings. Understanding that these drawings depict only typical embodiments of the disclosure and are not therefore to be considered to be limiting of its scope, the disclosure will be described and explained with additional specificity and detail through the use of the accompanying drawings, in which.

DETAILED DESCRIPTION

Reference throughout this specification to "one embodiment," "an embodiment," or similar language means that a particular feature, structure, or characteristic described in connection with the embodiment is included in at least one embodiment of the present disclosure. Thus, appearances of the phrases "in one embodiment," "in an embodiment," and similar language throughout this specification may, but do not necessarily, all refer to the same embodiment.

Furthermore, the described features, structures, or characteristics of the disclosure may be combined in any suitable manner in one or more embodiments. In the following description, numerous specific details are provided for a thorough understanding of embodiments of the disclosure. One skilled in the relevant art will recognize, however, that the disclosure may be practiced without one or more of the specific details, or with other methods, components, materials, and so forth. In other instances, well-known structures, materials, or operations are not shown or described in detail to avoid obscuring aspects of the disclosure.

The schematic flow chart diagrams included herein are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

Figure 1:
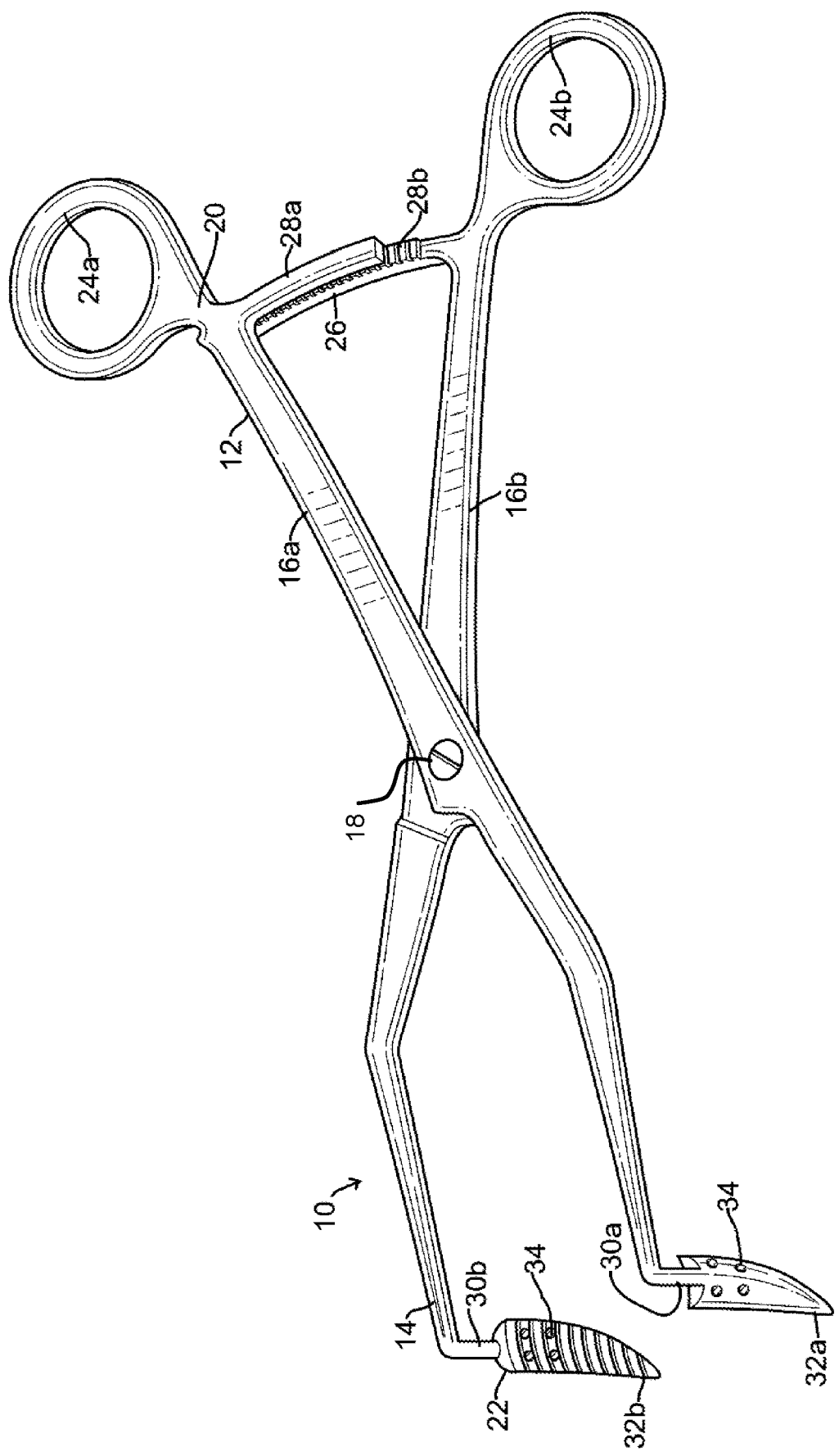
FIG. 1 is a perspective view illustrating one embodiment of a surgical clamp for Lapidus bunion surgery.

FIG. 1 depicts one embodiment of a surgical clamp 10 for Lapidus bunion surgery. Broadly, in certain embodiments, a surgical clamp 10 may comprise a handheld, hinged instrument used for grasping and holding objects or tissue during surgery. The surgical clamp 10 may be constructed and/or arranged to hold a portion of a foot in a corrected inter-metatarsal angle and/or a first metatarsal frontal plane rotation during a bunion surgery, or the like.

In an exemplary embodiment, the surgical clamp 10 may be used to correct the first metatarsal position by hooking around the first metatarsal neck and second and/or third metatarsal necks and closing down the pathological angle and may operate to hold the correction in one or more planes (e.g., all planes) during the surgery. The surgical clamp 10 may allow for motion of the first metatarsophalangeal (MTP) joint, fluoroscopy imaging, intra-operative X-ray imaging, and permanent fixation, all while holding the proper correction, and remaining out of the way of the surgical workspace during a surgical procedure.

In an exemplary embodiment, the surgical clamp 10 may comprise a proximal portion 12 and a distal portion 14. In some embodiments, the surgical clamp may comprise a first branch 16a and a second branch 16b. The surgical clamp 10 may further comprise a proximal handle 20 and distal gripper 22. The proximal handle 20 may further comprise proximal portions of the first branch 16a and the second branch 16b, a first ring 24a, and a second ring 24b, or the like. The proximal handle 20 may be provided with a lock 26. In the depicted embodiment, the lock 26 assumes the form of lugs 28a, 28b, provided with pawls. Each of the branches 16a, 16b may hold a lug 28a, 28b oriented toward the lug 28a, 28b of the other branch 28b, 28a. The lugs 28a, 28b may comprise two surfaces provided with pawls cooperating one against the other when the branches 16a, 16b are in a closed position. The surfaces may perform a rack function and may make it possible to keep the surgical clamp 10 closed and under pressure.

In another embodiment, the lock 26 may comprise a threaded arm that extends from the first branch 16a, through an opening in the second branch 16b, with a complementary threaded knob on an opposite side of the second branch 16b, which may be twisted around the threaded arm to tighten, loosen, and/or otherwise adjust a relative position of the second branch 16b relative to the first branch 16a, selectively fixing the relative position, or the like. In a further embodiment, the lock 26 may comprise a swinging bar coupled to the first branch 16a which is selectively couplable to a slot disposed on the second branch 16b to fix the relative position of the opposing branches 16a, 16b relative to each other. Other embodiments may include other types of locks 26 between the opposing branches 16a, 16b to selectively fix a relative position of the opposing branches so that the first and second grippers 22 may selectively hold a position of a first metatarsal relative to a different metatarsal (e.g., the second metatarsal, the third metatarsal, or the like).

At the distal portion 14 of the clamp 10, the branches 16a, 16b may further comprise substantially perpendicular distal end portions 30a, 30b. The distal gripper 22 may comprise substantially vertical serrated spoons 32a, 32b mounted to and extending substantially vertically from substantially perpendicular distal end portions 30a, 30b. The substantially vertical serrated spoons 32a, 32b may have a special shape, to hook around and/or grip a first metatarsal neck and a different metatarsal neck (e.g., of a second metatarsal, a third metatarsal, or the like). In some embodiments, the first and/or second grippers 22, 32a, 32b may be formed to extend at a non-zero angle away from the opposing branches 16a, 16b (e.g., out of a plane in which the opposing branches 16a, 16b pivot, substantially perpendicular to the opposing branches 16a, 16b, about a ninety degree angle, between about an eighty degree and a one hundred degree angle, between about a seventy degree and a one hundred and ten degree angle, between about a forty-five degree angle and a one hundred and thirty-five degree angle, or other non-zero angle). Because of the non-zero angle, in certain embodiments, the opposing branches 16a, 16b and the handles 20, 24a, 24b may extend over the toes and away from the foot, out of the way of the surgery and any other surgical equipment, or the like.

Figure 2:
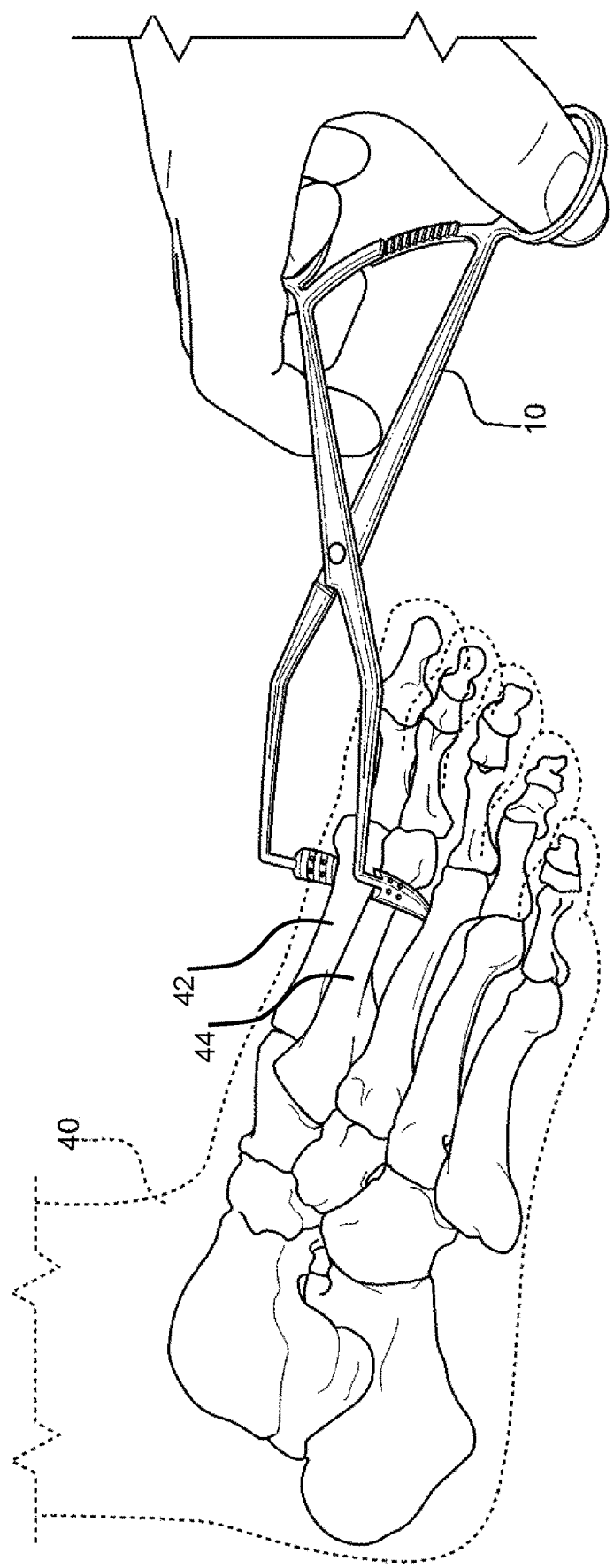
FIG. 2 is a perspective view illustrating one embodiment of a system for Lapidus bunion surgery.
Figure 3:
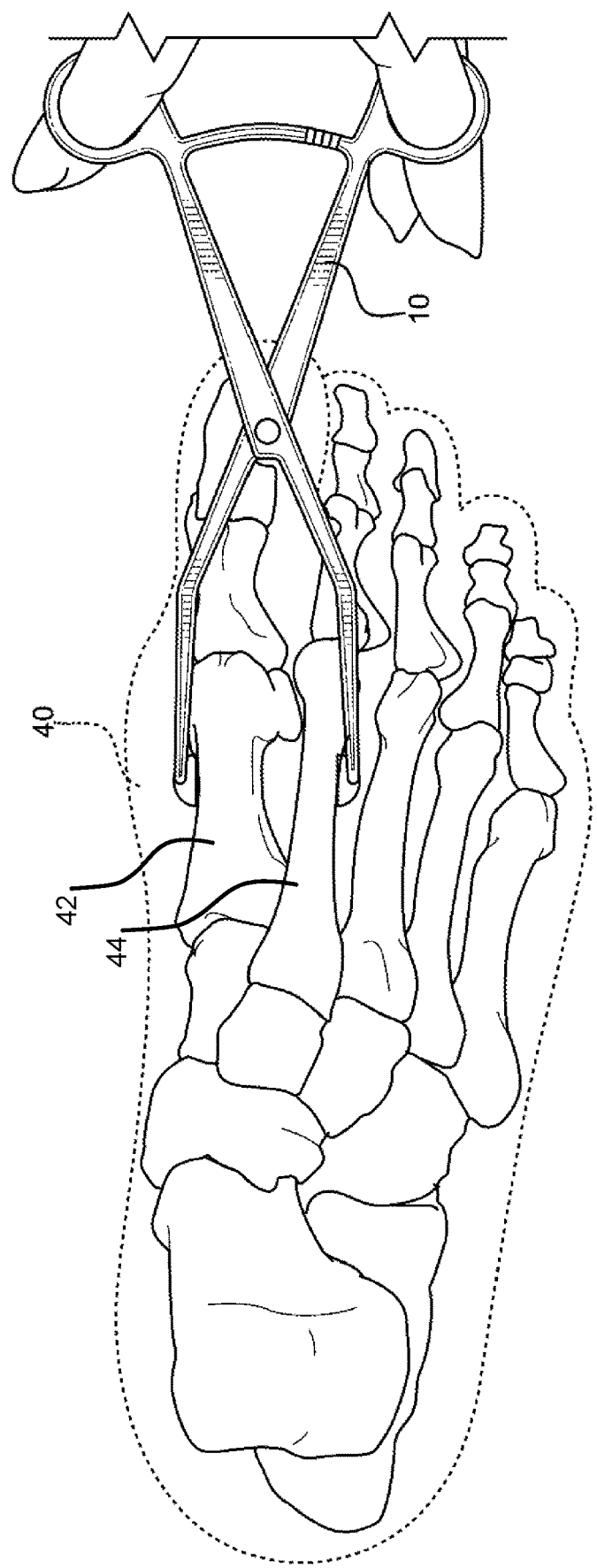
FIG. 3 is a top view illustrating a further embodiment of a system for Lapidus bunion surgery.

FIG. 2 and FIG. 3 depict embodiments of systems for Lapidus bunion surgery on a foot 40 using a surgical clamp 10. As seen at FIGS. 2-3, the substantially vertical serrated spoons 32a, 32b may be constructed and arranged to act as jaws which grip and immobilize the bones in a desired corrected position while keeping the entire surgical clamp 10 out of the way of fixation devices. The substantially vertical serrated spoons 32a, 32b may further comprise an interface provided with teeth so as to ensure satisfactory gripping of the structures to maintain the correction during the surgical procedures as described hereinabove. Advantageously, the interfaces of the substantially vertical serrated spoons 32a, 32b may have complementary shapes. Further, the inner surfaces of the substantially vertical serrated spoons 32a, 32b may comprise a plurality of teeth 34 to ensure satisfactory gripping during surgery.

In some embodiments, the spoons 32a, 32b may further comprise one or more holes or openings (e.g., which may be drilled into them, molded, or provided by any suitable means), the one or more holes being constructed and arranged to accommodate placement of a wire (e.g., k-wire or the like) therethrough to hold position and/or for rotation of the surgical clamp 10, of the first metatarsal 42, or the like, if needed. The two substantially vertical serrated spoons 32a, 32b are movable in response to movement of the branches 28a, 28b by the rings 24a, 24b or other handles 20 (e.g., opposing handles 20 with or without rings 24a, 24b), or the like. For example, the surgical clamp 10 may include a hinge 18 disposed at an intersection of the opposing branches 16a, 16b, and the branches 16a, 16b may rotate and/or pivot, within a plane, about an axis of the hinge 18 in response to actuation of the handles 20 (e.g., a user's movement of the rings 24a, 24b, or other opposing handles 20). A hinge 18 may include a pin, screw, bar, fulcrum, or other axis coupling the opposing branches 16a, 16b at the intersection.

The surgical clamp 10, in various embodiments, may be made of any suitable material by any suitable process. For example, without limitation, the surgical clamp may be reusable and engineered and made out of surgical stainless steel or another metallic material by a machinist or a medical device company. In one embodiment, the surgical clamp 10 may comprise a polymer material (e.g., the surgical clamp 10 may be disposable, one-time-use for a single surgery, or the like), such as an acrylonitrile butadiene styrene (ABS), a polycarbonate plastic, a polydicyclopentadiene plastic (pDCPD), a polybutylene terephthalate (PBT), a polysulfone (PSU), a polyphenylsulfone (PPSU), a polyamide (PA), a polyarylamide, a polysiloxane, a polyphosphazene, a high-density polyethylene (HDPE), a polypropylene (PP), a polychlorotrifluoroethylene (PCTFE), a polymer blend, or the like.

It may be difficult to position and/or hold the first metatarsal 42 in proper corrected position during a Lapidus bunion surgery. The bone may need to be moved, and held in the proper place, temporarily during the surgery, until permanent fixation is applied. The surgical clamp 10 may be out of the way of other surgical instruments during surgery and allow for motion of the great toe joint, to solve this problem.

In an exemplary embodiment, the surgical clamp 10 may be constructed and/or arranged to accomplish several things. The surgical clamp 10 may reduce, and/or correct, the first metatarsal 42 angle to at or near normal. The surgical clamp 10 may also hold the correction in multiple planes (e.g., both the sagittal and frontal planes, in all planes, or the like). Further, the surgical clamp 10 may provide its function while being located out of the way of other instruments (e.g., extending over the toes and away from the foot) and far enough away from the surgical site to allow room to perform the surgery. In addition, the surgical clamp 10 may also allow dorsiflexion of the first metatarsal 42/phalangeal joint during the surgery. The surgical clamp 10 may also be out of the way of interoperative X-ray devices, may be formed of a material substantially transparent to X-rays, or the like.

The surgical clamp 10 may be specifically designed, shaped, and made for a Lapidus bunion surgery, with the proper length and specific first and second grippers 22 formed to hook around and grip necks of the first metatarsal 42 and second or third metatarsals 44. The surgical clamp 10 may hold the first metatarsal bone 42 in correction while the surgery is performed and may be constructed and/or arranged to remain out of the way of other instruments, the joint, and/or an X-ray machine.

Other clamps may not be capable of holding the bone in the proper position in the sagittal or frontal plane. Further, other clamps may be oriented during surgery in a manner in which they remain in the surgical field in the way of the surgeon, and/or may not allow the first metatarsal 42 phalangeal joint to move as needed during surgery.

The surgical clamp 10 may correct the first metatarsal 42 position by hooking around and gripping the first metatarsal 42 neck and second or third metatarsal 44 neck and closing down the pathological angle, maintaining the correction in all planes during the surgery. The surgical clamp 10 may permit first metatarsal 42 phalangeal joint motion while it holds the proper correction, and concurrently allow for fluoroscopy imaging, intra-operative X-ray imaging, and/or permanent fixation, while it may also be retained out of the way of the surgeon's workspace.

In an exemplary embodiment, the surgical clamp 10 comprises a Lapidus bunionectomy clamp 10 with first and second grippers 22 comprising substantially vertical serrated spoons 32a, 32b to hold correction (e.g., with a concave curvature oriented toward the first metatarsal 42 and a different metatarsal 44 to hook around and grip the bones 42, 44). In one embodiment, the spoons 32a, 32b at the distal tip 14 of the surgical clamp 10 comprise a special shape constructed and arranged to grip and immobilize the bones 42, 44 in a desired corrected position while keeping the entire surgical clamp 10 out of the way of another fixation device and/or surgical instrument.

In use, in accordance with one embodiment, the surgical clamp 10 may be used as follows. The surgical clamp 10 may be placed on the first metatarsal 42 and a different metatarsal 44 (e.g., the second or third metatarsal 44) during bunion correction. The first metatarsal 42 may be rotated in the frontal plane to a proper position, and the surgical clamp 10 may engage and/or close down the angle between the first metatarsal 42 and the different metatarsal 44 to normal. The surgical clamp 10 may hold the corrected position in both the frontal and sagittal planes throughout the procedure. The surgical clamp 10 may be constructed and/or arranged to have a length sufficient to be retained out of the way of the first metatarsal 42 joint to allow motion thereof. The surgical clamp 10 may be left in place to hold the correction during final fixation placement, or the like.

Figure 4:
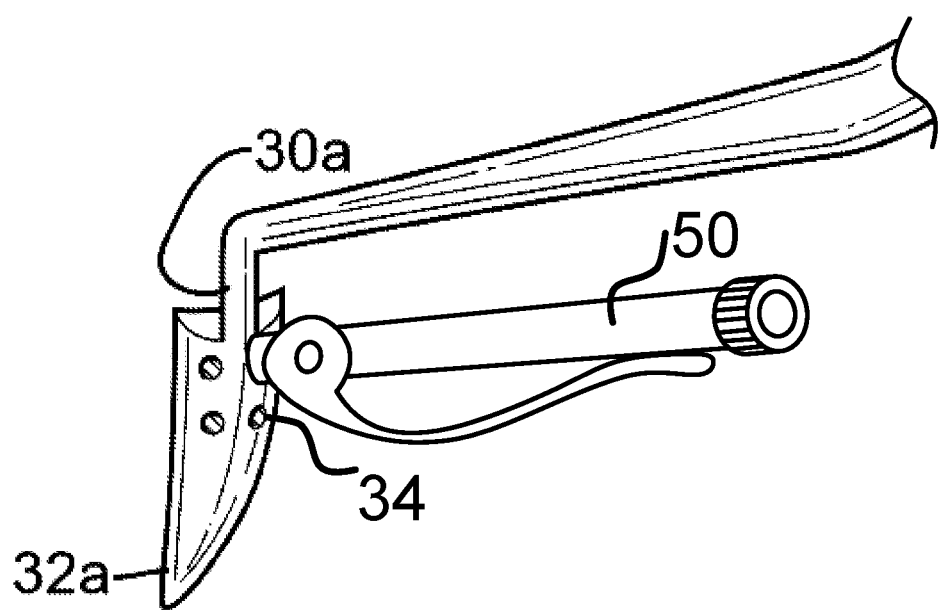
FIG. 4 is a perspective view illustrating one embodiment of wire feeding hardware.

FIG. 4 depicts one embodiment of wire feeding hardware 50 for a surgical clamp 10. The wire feeding hardware 50, in the depicted embodiment, is coupled (e.g., welded, glued, threaded and screwed into, formed from the same continuous material of, or otherwise coupled) to a hole 34 of a serrated spoon 32a or other gripper 22. A hole 34 may be shaped and position to receive a wire (e.g., a k-wire or the like). The wire feeding hardware 50 coupled to at least one hole 34, in the depicted embodiment, comprises a tube shaped to receive the wire, and may include additional hardware for locking the wire in place (e.g., a lever to selectively pinch and secure the wire within the tube or the like), drive the wire through the hole 34 and/or through bone of the first metatarsal 42 (e.g., a manual drill and/or driver, an electric drill and/or driver, or the like), retract the wire from the hole 34 and/or the bone of the first metatarsal 42, and/or otherwise manipulate the wire.

Wire and/or wire feeding hardware 50, in some embodiments, may assist in rotating the first metatarsal 42, locking a rotation of the first metatarsal 42, holding a position of the surgical clamp 10 (e.g., so it doesn't slide off the bone), or the like. In one embodiment, the wire feeding hardware 50 may be removable and installable in a hole 34 on either of the first or second serrated spoons 32a, 32b, such that the surgical clamp 10 and wire feeding hardware 50 may be used on either the left of the right foot. In another embodiment, the wire feeding hardware 50 may be permanently or semi-permanently coupled to a hole 34 of a serrated spoon 32a, 32b (e.g., the serrated spoon 32a, 32b corresponding to the first metatarsal 42 of the foot on which the surgery is occurring, with different surgical clamps 10 for left and right feet. In embodiments where a surgical clamps 10 are designed specifically for a left or a right foot, a serrated spoon 32a, 32b or other gripper 22 corresponding to a different metatarsal 44 (e.g., a second metatarsal 44, a third metatarsal 44, or the like) may be smaller, with a different shape (e.g., different curvature, different angle, different location of holes 34, or the like) corresponding to the different metatarsal 44 than the serrated spoon 32a, 32b or other gripper 22 corresponding to the first metatarsal 42.

Figure 5:
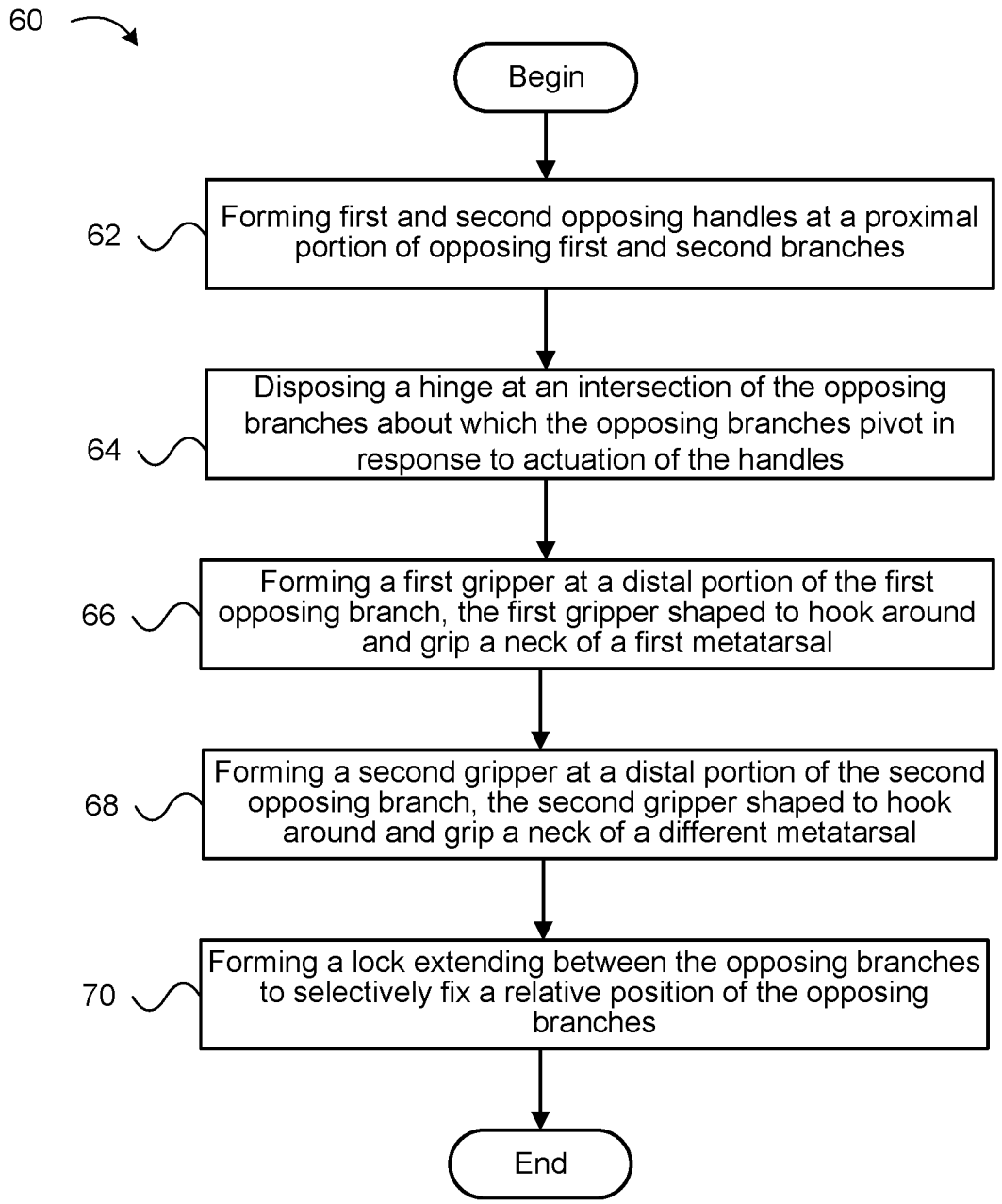
FIG. 5 is a schematic block diagram illustrating one embodiment of a method for a surgical clamp for Lapidus bunion surgery.

FIG. 5 depicts one embodiment of a method 60 for manufacturing a surgical clamp 10 for Lapidus bunion surgery. A manufacturer, as used herein, may comprise one or more of a hardware manufacturing device, a human worker, or the like.

The method 60 begins and a manufacturer forms 62 first and second opposing handles 20, 24a, 24b at a proximal portion 12 of opposing first and second branches 16a, 16b. A manufacturer disposes 64 a hinge 18 at an intersection of the opposing branches 16a, 16b about which the opposing branches 16a, 16b pivot in response to actuation of the handles 20, 24a, 24b.

A manufacturer forms 66 a first gripper 22, 32a at a distal portion 14 of the first opposing branch 16a (e.g., the first gripper 22, 32a may be shaped to hook around and grip a neck of a first metatarsal 42, a different metatarsal 44, or the like). A manufacturer forms 68 a second gripper 22, 32b at a distal portion 14 of the second opposing branch 16b (e.g., the second gripper 22, 32b may be shaped to hook around and grip a neck of a first metatarsal 42, a different metatarsal 44, or the like). In some embodiments, the first and/or second grippers 22, 32a, 32b may be formed to extend at a non-zero angle away from the opposing branches 16a, 16b (e.g., substantially perpendicular to the opposing branches 16a, 16b, about a ninety degree angle, between about an eighty degree and a one hundred degree angle, between about a seventy degree and a one hundred and ten degree angle, between about a forty-five degree angle and a one hundred and thirty-five degree angle, or other non-zero angle).

A manufacturer forms 70 a lock 26 extending between the opposing branches 16a, 16b to selectively fix a relative position of the opposing branches 16a, 16b so that the first and second grippers 22, 32a, 32b are configured to selectively hold a position of the first metatarsal 42 relative to the different metatarsal 44 and the method 60 ends.

Figure 6:
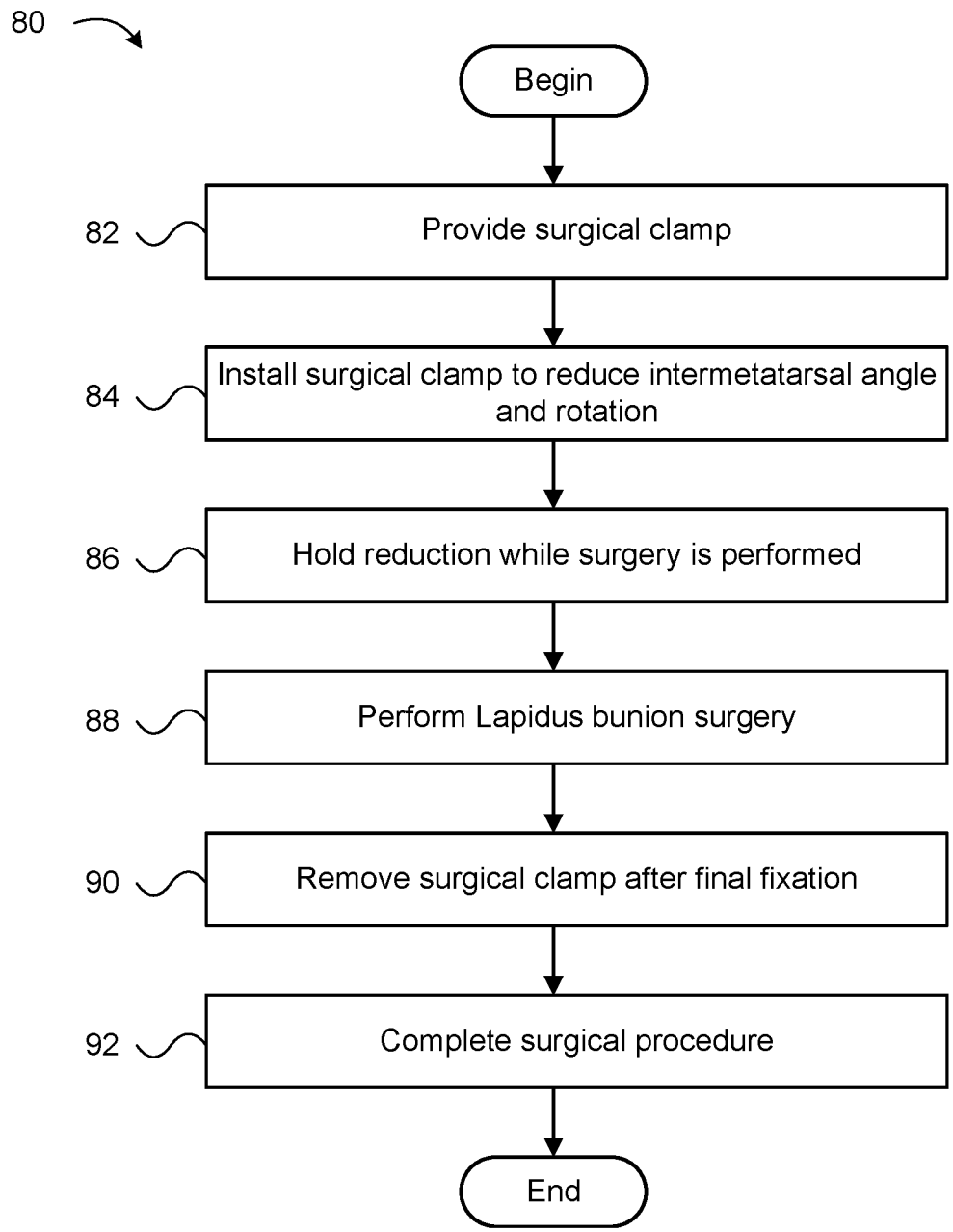
FIG. 6 is a schematic block diagram illustrating one embodiment of a method for Lapidus bunion surgery.

FIG. 6 depicts one embodiment of a method 80 for Lapidus bunion surgery. The method 80 begins and a user (e.g., a surgeon, doctor, or other user) provides 82 a surgical clamp 10; installs 84 the surgical clamp 10 in place in a body on which the Lapidus bunion surgery is being performed, so that the surgical clamp 10 may reduce an intermetatarsal angle and rotation or the like; holds 86 the reduction while the surgery is performed; performs 88 the Lapidus bunion surgery; removes 90 the surgical clamp 10 after the final fixation of the surgery is accomplished; completes 92 the surgical procedure; and the method 80 ends. The method 80 may further comprise cleaning and/or sterilizing the surgical clamp 10, using the surgical clamp 10 in another procedure, recycling and/or disposing of a one-time-use surgical clamp 10, or the like.

A means for pivoting opposing first and second branches 16a, 16b of a surgical clamp 10 about an axis 18 from a proximal end 12 of the opposing first and second branches 16a, 16b, in various embodiments, may include one or more of a handle 20, a ring 24a, 24b, a grip, an actuator, a lever, an arm, a branch 16a, 16b, and/or the like. Other embodiments may include similar or equivalent means for pivoting opposing first and second branches 16a, 16b of a surgical clamp 10 about an axis 18 from a proximal end 12 of the opposing first and second branches 16a, 16b.

A means for hooking around and gripping a neck of a first metatarsal 42 from a distal end 14 of a first branch 16a at a non-zero angle with the first branch 16a, in various embodiments, may include one or more of a gripper 22, a serrated spoon 32a, a jaw, a clamp, a tooth, a hook, a plier, a tong, an extension, a branch, an arm, and/or the like. Other embodiments may include similar or equivalent means for hooking around and gripping a neck of a first metatarsal 42 from a distal end 14 of a first branch 16a at a non-zero angle with the first branch 16a.

A means for hooking around and gripping a neck of a different metatarsal 44 from a distal end 14 of a second branch 16b at a non-zero angle with the second branch 16b, in various embodiments, may include one or more of a gripper 22, a serrated spoon 32a, a jaw, a clamp, a tooth, a hook, a plier, a tong, an extension, a branch, an arm, and/or the like. Other embodiments may include similar or equivalent means for hooking around and gripping a neck of a different metatarsal 44 from a distal end 14 of a second branch 16b at a non-zero angle with the second branch 16b.

A means for selectively fixing a relative position of opposing branches 16a, 16b and/or for selectively holding a position of a first metatarsal 42 relative to a different metatarsal 44, in various embodiments, may include one or more of a lock 26, a lug 28a, 28b, a pawl, a rack, a threaded arm, a threaded knob, a swinging bar, a slot, a bolt, a nut, a screw, a clip, a clamp, a chain, a clasp, and/or the like. Other embodiments may include similar or equivalent means for selectively fixing a relative position of opposing branches 16a, 16b and/or for selectively holding a position of a first metatarsal 42 relative to a different metatarsal 44.

A means for locking, driving, and/or retracting a wire through a hole 34 and/or through a first metatarsal 42, in various embodiments, may include one or more of wire feeding hardware 50, a tube, a pipe, a driver, a drill, a lever, a clamp, a knob, a screw, and/or the like. Other embodiments may include similar or equivalent means for locking, driving, and/or retracting a wire through a hole 34 and/or through a first metatarsal 42.

In summary, in one embodiment, the claim may be used for Lapidus bunion surgery. The surgical clamp 10 may be constructed and/or arranged to hold a correct intermetatarsal angle and first metatarsal 42 frontal plane rotation during bunion surgery. In use, an exemplary embodiment of the surgical clamp 10 may correct the first metatarsal 42 position by hooking around the first metatarsal 42 neck and second metatarsal 44 neck, and closing down the pathological angle, holding the correction in all planes during the surgery. In an exemplary embodiment, the surgical clamp 10 may be constructed and/or arranged to allow, while in use during surgery, first metatarsal 42/phalangeal joint motion, fluoroscopy imaging, intra-operative X-ray imaging, and/or permanent fixation, while maintaining the properly corrected conformation and while being held out of the way of the surgical workspace. In other embodiments, the surgical clamp 10 may be used to perform other surgeries, such as to reduce lesser Metatarsal metatdductus, in addition to bunions, or the like. For example, the surgical clamp 10 may clamp around any lesser metatarsal 144 and move the bones to a rectus alignment, or the like.

The present disclosure may be embodied in other specific forms without departing from its spirit or essential characteristics. The described embodiments are to be considered in all respects only as illustrative and not restrictive. The scope of the disclosure is, therefore, indicated by the appended claims rather than by the foregoing description. All changes which come within the meaning and range of equivalency of the claims are to be embraced within their scope.

What is claimed is:

1. A surgical clamp for Lapidus bunion surgery, the surgical clamp comprising:

first and second opposing handles disposed at a proximal portion of opposing first and second branches of a surgical clamp;
a hinge disposed at an intersection of the opposing branches about which the opposing branches pivot within a plane in response to actuation of the handles;
a first gripper disposed at a distal portion of the first opposing branch, the first gripper shaped to hook around and grip a neck of a first metatarsal;
a second gripper disposed at a distal portion of the second opposing branch, the second gripper shaped to hook around and grip a neck of a different metatarsal, the first and second grippers extending out of the plane in which the opposing branches pivot at a non-zero angle of at least forty-five degrees away from the opposing branches thereby extending the first and second opposing branches over toes and away from a foot of the first metatarsal and the different metatarsal; and
a lock extending between the opposing branches and selectively fixing a relative position of the opposing branches such that the first and second grippers selectively reduce an intermetatarsal angle of the first metatarsal relative to the different metatarsal and hold a frontal plane rotation of the first metatarsal.

2. The surgical clamp of claim 1, further comprising one or more holes disposed in at least one of the first and second grippers, the one or more holes shaped and positioned to receive wire.

3. The surgical clamp of claim 2, further comprising wire feeding hardware coupled to at least one hole of the one or more holes, the wire feeding hardware comprising a tube shaped to receive the wire and configured to one or more of lock the wire, drive the wire through the at least one hole, and retract the wire from the at least one hole.

4. The surgical clamp of claim 2, wherein the wire passes through the one or more holes and through bone of at least the first metatarsal thereby holding a rotation of the first metatarsal.

5. The surgical clamp of claim 1, wherein the first and second grippers selectively hold the position of the first metatarsal relative to the different metatarsal in multiple planes.

6. The surgical clamp of claim 5, wherein the first and second grippers selectively hold the position of the first metatarsal relative to the different metatarsal in at least the frontal and sagittal planes.

7. The surgical clamp of claim 1, wherein the first and second grippers selectively hold the position of the first metatarsal relative to the different metatarsal and a rotation of the first metatarsal.

8. The surgical clamp of claim 1, wherein the first and second grippers are shaped to allow dorsiflexion of a phalangeal joint of the first metatarsal while selectively holding the position of the first metatarsal relative to the different metatarsal.

9. The surgical clamp of claim 1, wherein the first and second grippers comprise serrated spoons shaped to hook around and grip the necks of the first metatarsal and the different metatarsal.

10. The surgical clamp of claim 1, wherein the non-zero angle at which the first and second grippers extend away from the opposing branches comprises a substantially perpendicular angle.

11. The surgical clamp of claim 1, wherein the lock comprises a complimentary pair of lugs with pawls cooperating against each other to perform a rack function to selectively fix the relative position of the opposing branches.

12. The surgical clamp of claim 1, wherein the lock comprises a threaded arm and the relative position is fixed by twisting a complimentary threaded knob around the threaded arm.

13. The surgical clamp of claim 1, wherein the surgical clamp comprises a polymer material and the surgical clamp is a disposable, one-time-use surgical clamp.

14. The surgical clamp of claim 1, wherein the second gripper is smaller than the first gripper with a different shape than the first gripper such that the second gripper corresponds specifically to the different metatarsal and the surgical clamp is shaped for use with one of a left foot and a right foot.

15. The surgical clamp of claim 1, wherein the non-zero angle of the first and second grippers extends the first and second opposing branches over the toes and away from the foot of the first metatarsal and the different metatarsal out of the way of a surgery on the foot.

16. The surgical clamp of claim 1, wherein the different metatarsal comprises one of a second metatarsal and a third metatarsal.

17. An apparatus comprising:
means for pivoting, within a plane, opposing first and second branches of a surgical clamp about an axis from a proximal end of the opposing first and second branches;
means for hooking around and gripping a neck of a first metatarsal from a distal end of the first branch at a non-zero angle with the first branch of at least seventy degrees out of the plane in which the first and second branches pivot;
means for hooking around and gripping a neck of a different metatarsal from a distal end of the second branch at a non-zero angle with the second branch of at least seventy degrees out of the plane in which the first and second branches pivot; and
means for selectively fixing a relative position of the opposing branches and for selectively holding a position of the first metatarsal relative to the different metatarsal thereby reducing an intermetatarsal angle of the first metatarsal relative to the different metatarsal and holding a frontal plane rotation of the first metatarsal.

18. The apparatus of claim 17, further comprising means for one or more of locking a wire, driving a wire, and retracting a wire through the first metatarsal.

19. A method comprising:
forming first and second opposing handles at a proximal portion of opposing first and second branches;
disposing a hinge at an intersection of the opposing branches about which the opposing branches pivot within a plane in response to actuation of the handles;
forming a first gripper at a distal portion of the first opposing branch, the first gripper shaped to hook around and grip a neck of a first metatarsal;
forming a second gripper at a distal portion of the second opposing branch, the second gripper shaped to hook around and grip a neck of a different metatarsal, the first and second grippers extending out of the plane in which the opposing branches pivot at a non-zero angle of at least forty-five degrees away from the opposing branches thereby extending the first and second opposing branches over toes and away from a foot of the first metatarsal and the different metatarsal;
forming one or more holes in at least one of the first and second grippers; and forming a lock extending between the opposing branches to selectively fix a relative position of the opposing branches such that the first and second grippers are configured to selectively hold a position of the first metatarsal relative to the different metatarsal.

20. The method of claim 19, further comprising:

coupling wire feeding hardware to at least one hole of the one or more holes.

\* \* \* \* \*